United States Patent
Mendelovici et al.

(10) Patent No.: US 7,067,669 B2
(45) Date of Patent: Jun. 27, 2006

(54) SUBSTANTIALLY PURE CILOSTAZOL AND PROCESSES FOR MAKING SAME

(75) Inventors: Marioara Mendelovici, Rehovot (IL); Nina Finkelstein, Herzliya (IL); Gideon Pilarski, Holon (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 0 days.

(21) Appl. No.: 11/300,862

(22) Filed: Dec. 14, 2005

(65) Prior Publication Data

US 2006/0094756 A1 May 4, 2006

Related U.S. Application Data

(60) Division of application No. 10/951,570, filed on Sep. 27, 2004, which is a continuation of application No. 10/336,721, filed on Jan. 6, 2003, now Pat. No. 6,825,214, which is a continuation-in-part of application No. 09/929,683, filed on Aug. 14, 2001, now Pat. No. 6,515,128.

(60) Provisional application No. 60/190,588, filed on Mar. 20, 2000, provisional application No. 60/225,362, filed on Aug. 14, 2000.

(51) Int. Cl.
*C07D 216/36* (2006.01)

(52) U.S. Cl. ....................................................... 546/158
(58) Field of Classification Search ................. 546/158
See application file for complete search history.

(56) References Cited

U.S. PATENT DOCUMENTS

| 4,277,479 A | 7/1981 | Nishi et al. |
| 6,531,603 B1 | 3/2003 | Stowell et al. |
| 2002/0137936 A1 | 9/2002 | Mendelovici et al. |

FOREIGN PATENT DOCUMENTS

| JP | 09124605 | 5/1997 |
| JP | 10330262 | 12/1998 |
| JP | 2000-229944 | 8/2000 |

*Primary Examiner*—Patricia L. Morris
(74) *Attorney, Agent, or Firm*—Kenyon & Kenyon LLP

(57) ABSTRACT

The present invention provides substantially pure cilostazol. The present invention also provides cilostazol particles that have reduced particle size.

8 Claims, No Drawings

SUBSTANTIALLY PURE CILOSTAZOL AND PROCESSES FOR MAKING SAME

RELATED APPLICATIONS

This application is a divisional application of U.S. application Ser. No. 10/951,570, filed on Sep. 27, 2004, which is a continuation of application Ser. No. 10/336,721, filed on Jan. 6, 2003, now U.S. Pat. No. 6,825,214, which is a continuation-in-part of application Ser. No. 09/929,683 filed on Aug. 14, 2001, now U.S. Pat. No. 6,515,128 which claims benefit of U.S. provisional application Nos. 60/190,588, filed on Mar. 20, 2000 and 60/225,362, filed on Aug. 14, 2000.

FIELD OF THE INVENTION

The present invention relates to processes for preparing cilostazol.

BACKGROUND OF THE INVENTION

The present invention pertains to processes for preparing 6-[4-(1-cyclohexyl-1H-tetrazol-5-yl)butoxy]-3,4-dihydro-2(1H)-quinolinone of formula (I)

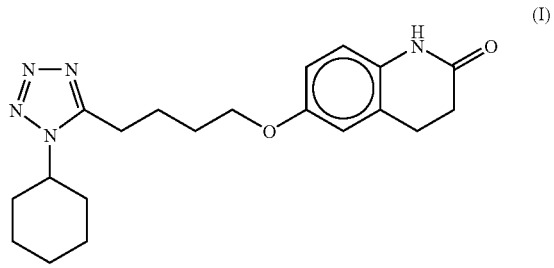

which is also known by the generic name cilostazol. Cilostazol inhibits cell platelet aggregation and is used to treat patients with intermittent claudication.

Cilostazol is described in U.S. Pat. No. 4,277,479 ("the '479 patent"), which teaches a preparation wherein the phenol group of 6-hydroxy-3,4-dihydroquinolinone ("6-HQ") of formula (II) is alkylated with a 1-cyclohexyl-5-(4-halobutyl)-tetrazole ("the tetrazole") of formula (III). It is recommended to use an equimolar or excess amount up to two molar equivalents of the tetrazole (III).

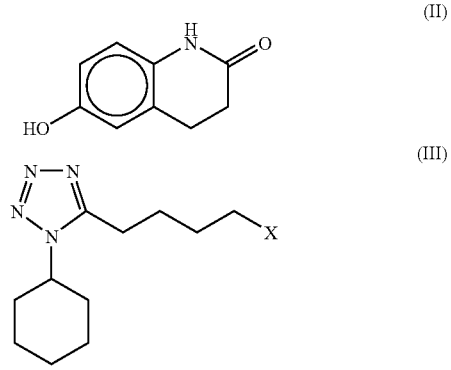

The '479 patent mentions a wide variety of bases that may be used to promote the alkylation reaction, namely, sodium hydroxide, potassium hydroxide, sodium carbonate, potassium carbonate, sodium bicarbonate, potassium bicarbonate, silver carbonate, elemental sodium, elemental potassium, sodium methylate, sodium ethylate, triethylamine, pyridine, N,N-dimethylaniline, N-methylmorpholine, 4-dimethylaminopyridine, 1,5-diaza-bicyclo[4,3,0]-non-5-ene, 1,5-diazabicyclo[5,4,0]-undec-7-ene ("DBU"), and 1,4-diazabicyclo[2,2,2]octane.

The '479 patent states that the alkylation may be conducted neat or in solvent. Suitable solvents are said to be methanol, ethanol, propanol, butanol, ethylene glycol, dimethyl ether, tetrahydrofuran, dioxane, monoglyme, diglyme, acetone, methylethylketone, benzene, toluene, xylene, methyl acetate, ethyl acetate, N,N-dimethylformamide, dimethylsulfoxide and hexamethylphosphoryl triamide.

According to Examples 4 and 26 of the '479 patent, cilostazol was prepared using DBU as base and ethanol as solvent.

In Nishi, T. et al. *Chem. Pharm. Bull.* 1983, 31, 1151–57, a preparation of cilostazol is described wherein 6-HQ is reacted with 1.2 molar equivalents of 5-(4-chlorobutyl)-1-cyclohexyl-1H-tetraazole ("CHCBT," tetrazole III wherein X=Cl) in isopropanol with potassium hydroxide as base. Cilostazol was obtained in 74% yield.

One reason for using an excess of tetrazole as was done in Nishi et al. and recommended by the '479 patent is that CHCBT is unstable to some bases. When exposed to an alkali metal hydroxide in water for a sufficient period, CHCBT undergoes elimination and cyclization to yield byproducts (IV) and (V).

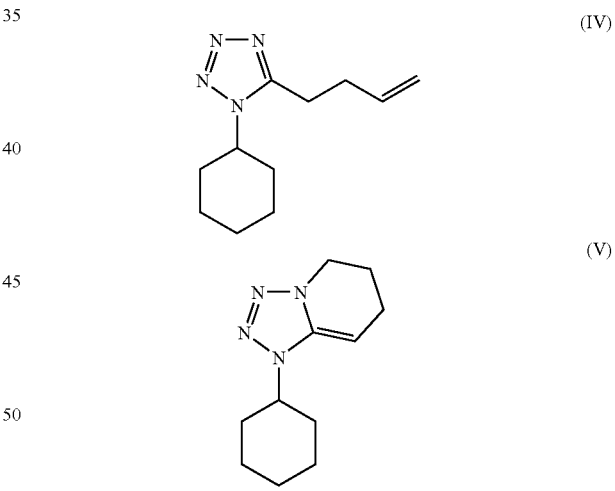

Nishi et al.'s reported yield is based upon the limiting reagent 6-HQ. The yield with respect to CHCBT is 69%. In the economics of producing a chemical on a large scale, improvements in chemical yield are rewarded with savings in the chemical's production cost. CHCBT is an expensive compound to prepare and should not be wasted. It would be highly desirable to be able to realize further improvement in yield of the alkylation of 6-HQ with CHCBT and its halogen analogs in a way that lowers the cost of producing cilostazol. In other words, it would be desirable to further improve the yield of cilostazol by increasing the degree of conversion of CHCBT to cilostazol, as opposed to, for example, improving the yield calculated from 6-HQ by increasing the excess of tetrazole or manipulating the reaction conditions in a way that increases the conversion of 6-HQ to cilostazol but at the expense of poorer conversion of CHCBT to cilostazol.

Although CHCBT is unstable to hydroxide ion, it is relatively stable in the presence of non-nucleophilic organic bases. There are advantages to using inorganic bases, however, that favor their selection over organic bases. Firstly, the phenolic proton of 6-HQ is labile. Thus, relatively non-caustic and easily handled inorganic bases may be used to prepare cilostazol. Further, inorganic bases are easier to separate from the product and are less toxic to the environment when disposed than organic bases are. Therefore, it would also be highly desirable to use an inorganic base while realizing an improvement in conversion of CHCBT to cilostazol.

SUMMARY OF THE INVENTION

The present invention provides improved processes for preparing cilostazol (I) by alkylating the phenol group of 6-HQ with the δ carbon of a 5-(4-halobutyl)-1-cyclohexyl-1H-tetrazole.

In a first aspect, the invention provides a process wherein 6-HQ and a water soluble base are dissolved in water. A 1-cyclohexyl-5-(4-halobutyl)-tetrazole is dissolved in a water-immiscible organic solvent. The two solutions are combined in the presence of a quaternary ammonium salt phase transfer catalyst to form a biphasic mixture in which the 6-HQ and tetrazole react to produce cilostazol. The purity of the cilostazol may be detected by reversed-phase high performance liquid chromatography (HPLC) using gradient elution. The process may be practiced by a variety of procedures taught by the present invention. In one variation, a reaction promoter, like sodium sulfate, is added to accelerate phase transfer of 6-HQ into the organic solvent.

Another aspect of the present invention provides a preparation of cilostazol from a single phase reaction mixture of 6-HQ and a 1-cyclohexyl-5-(4-halobutyl)-tetrazole and a mixture of inorganic bases. The base mixture comprises an alkali metal hydroxide and alkali metal carbonate. This process minimizes decomposition of the starting tetrazole and cilostazol by buffering the pH which results in improved yield calculated based upon the tetrazole, the more precious of the two organic starting materials. A preferred embodiment wherein the alkali metal hydroxide is added portion-wise minimizes the formation of dimeric byproducts. In another preferred embodiment of the homogeneous process, the reaction mixture is dehydrated with molecular sieves before the tetrazole is added.

Yet another aspect of the present invention provides a pharmaceutical composition comprising substantially pure cilostazol obtained by the methods of the present invention described above. By "substantially pure" is meant having a purity equal to or greater than 98%.

Another aspect of the present invention provides a pharmaceutical composition comprising cilostazol particles of reduced particle size. By "reduced particle size" is meant about 90% of the particles having a diameter equal to or less than about 60 microns (d(0.9)≦60 microns). The reduced particle size may be obtained by fine-milling or micronization.

DETAILED DESCRIPTION OF THE INVENTION

The present invention provides a process for preparing cilostazol (I) by alkylating the phenol group of 6-HQ with the δ carbon of a 5-(4-halobutyl)-1-cyclohexyl-1H-tetrazole ("the tetrazole"). The transformation itself, depicted in Scheme 1 is known.

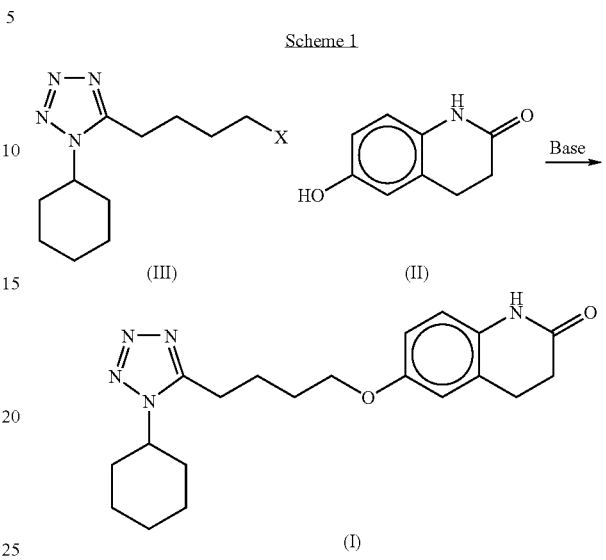

Scheme 1

The present invention improves upon processes previously used to perform the chemical transformation depicted in Scheme 1 which result in a greater conversion of the tetrazole starting material to cilostazol. The improvements may be viewed as falling into one of two aspects of the present invention: (1) a heterogeneous, or biphasic, process employing phase transfer catalysis and improvements applicable to the heterogeneous process and (2) improvements applicable to a homogeneous process.

In a first aspect, the present invention provides a biphasic process for preparing cilostazol by alkylating the phenol group of 6-HQ with a 5-(4-halobutyl)-1-cyclohexyl-1H-tetrazole using controlled phase transfer methodology. For a discussion of the theory and general application of phase transfer catalysis, See, Dehmlow, E. V.; Dehmlow, S. S., *Phase Transfer Catalysis* 3rd ed. (VCH Publishers: New York 1993).

According to the present inventive process, a solution of 6-HQ, a water-soluble base and a trialkyl ammonium phase transfer catalyst in water is contacted with a solution of a 5-(4-halobutyl)-1-cyclohexyl-1H-tetrazole in a water-immiscible organic solvent for a period of time sufficient to cause the tetrazole to be substantially completely converted to cilostazol and then separating the cilostazol from the biphasic mixture.

The biphasic reaction mixture separates the base from the base sensitive tetrazole. Although not intending to be bound by any particular theory, it is believed that the 6-HQ phenolate anion complexes with the tetra-alkyl ammonium ion which increases its solubility in the water-immiscible organic solvent. The complexed phenolate then enters the water-immiscible phase and reacts with the tetrazole there.

Suitable phase transfer catalysts are ammonium salts such as tricaprylylmethylammonium chloride (Aliquat® 336), tetra-n-butylammonium bromide ("TBAB"), benzyltriethylammonium chloride ("TEBA"), cetyltrimethylammonium bromide, cetylpyridinium bromide, N-benzylquininium chloride, tetra-n-butylammonium chloride, tetra-n-butylammonium hydroxide, tetra-n-butylammonium iodide, tetra-ethylammonium chloride, benzyltributylammonium bromide, benzyltriethylammonium bromide, hexadecyltriethylammonium chloride, tetramethylammonium chloride, hexadecyltrimethyl ammonium chloride, and octyltrimethylammonium chloride. More preferred phase transfer catalysts are Aliquat® 336, TBAB, TEBA and mixtures thereof, the most preferred being Aliquat® 336. The phase transfer catalyst may be used in a stoichiometric or substoichiometric amount, preferably from about 0.05 to about 0.25 equivalents with respect to the tetrazole.

Suitable bases are soluble in water but poorly soluble or insoluble in water-immiscible organic solvents. Such bases are typically metal salts of inorganic counterions. Preferred inorganic bases are hydroxide and carbonate salts of alkali metals. More preferred inorganic bases are NaOH, KOH, $K_2CO_3$, $Na_2CO_3$ and $NaHCO_3$. The most preferred inorganic base in the heterogeneous process is NaOH.

The halogen atom of 5-(4-halobutyl)-1-cyclohexyl-1H-tetrazole (X in formula III) may be chlorine, bromine or iodine, preferably chlorine. Although the tetrazole may be used in any amount desired, it is most desirable to use a stoichiometric amount of tetrazole or less relative to 6-HQ, more preferably about 0.9 molar equivalents.

Preferred water-immiscible solvents are toluene, hexanes, dichloromethane and mixtures thereof. An excess of water to water-immiscible solvent is preferred, although the ratio may vary widely. Preferred ratios of water to water-immiscible solvent range from about 0.5:1 to about 8:1 (v/v), more preferably from about 1:1 to about 6:1.

According to one preferred procedure for preparing cilostazol, the 6-HQ, water-soluble base and phase transfer catalyst are dissolved in water. The tetrazole is dissolved in the water-immiscible solvent and the two solutions are contacted and agitated, with optional heating, until the tetrazole is substantially consumed. Cilostazol may be isolated by cooling the reaction mixture to precipitate the cilostazol and then filtering or decanting the solutions. Cilostazol may be purified by methods shown in Table 1 or any conventional method known in the art, including, for example, RP-HPLC using gradient elution, as discussed above.

Alternatively, a biphasic mixture of the water-miscible organic solvent and the aqueous solution of 6-HQ, water-soluble base and the phase transfer catalyst is mixed and optionally heated while the tetrazole is slowly added to the stirred mixture. The slow addition of the tetrazole may be either continuous or portionwise.

In yet another alternative procedure, an aqueous suspension of 6-HQ and the phase transfer catalyst are contacted with the solution of tetrazole in the water-immiscible organic solvent. The biphasic mixture is agitated and optionally heated, while the water-soluble base is slowly added to the mixture. The slow addition may be either continuous as in a concentrated aqueous solution of the base or portionwise.

Each of these preferred procedures may be modified to take advantage of a further improvement, which is to add a reaction promoter to the aqueous phase. Reaction promoters are salts like sodium sulfate and potassium sulfate that increase the ionic strength of aqueous solutions but do not form strongly acidic or basic aqueous solutions. The reaction promoters decrease the solubility of 6-HQ in the aqueous phase and improve the efficiency of phase transfer to the organic phase. The preferred reaction promoter is sodium sulfate. Preferably, the reaction promoter is added in the amount of about 12–16% (w/v) with respect to the aqueous phase.

In a second aspect, the present invention provides a process for preparing cilostazol by alkylating the phenol group of 6-HQ with a 5-(4-halobutyl)-1-cyclohexyl-1H-tetrazole in a single liquid phase reaction mixture. 6-HQ and the tetrazole may be used in any amount, though it is preferred that the tetrazole be the limiting reagent, preferably used in from about 0.9 to about 0.99 equivalents with respect to the 6-HQ. Suitable solvents for forming the single liquid phase reaction mixture of this aspect of the invention are non-aqueous hydroxylic solvents, which include 1-butanol, isopropanol, 2-butanol and amyl alcohol.

In this process, two inorganic bases are used to catalyze the reaction. One of the bases is an alkali metal hydroxide such as sodium or potassium hydroxide. The other base is an alkali metal carbonate such as sodium or potassium carbonate. The most preferred alkali metal is potassium. Thus, preferred base mixtures are mixtures of potassium hydroxide and potassium carbonate. The alkali metal hydroxide is preferably used in an amount of from about 0.9 to about 1.2 equivalents with respect to the 6-HQ and the alkali metal carbonate is preferably used in an amount of about 0.1 to about 0.2 equivalents with respect to the 6-HQ.

The 6-HQ, tetrazole, alkali metal hydroxide and alkali metal carbonate may be added to the non-aqueous solvent in any order desired and at any rate desired.

In one preferred procedure, 6-HQ, the tetrazole and the alkali metal carbonate are added to the hydroxylic solvent along with a portion, e.g. about a one-fourth portion, of the alkali metal hydroxide. Thereafter, the remainder of the alkali metal hydroxide is added portionwise to the reaction mixture. It has been found that portionwise addition of the alkali metal hydroxide suppresses a byproduct that forms by the substitution of the halogen of the tetrazole by the 6-HQ lactam nitrogen.

Molecular sieves may be used to remove water from the single liquid phase reaction mixture before the tetrazole is added. Three and four angstrom molecular sieves are preferred, with three angstrom sieves being most preferred. The molecular sieves may be stirred with the solution to remove water formed by deprotonation of 6-HQ by KOH or adventitious water. Preferably, the molecular sieves are placed in a soxlet extraction funnel, the reservoir of a dropping funnel, or other suitable apparatus mounted on the reaction vessel that will allow circulation of vapor through the molecular sieves and return of the condensate to the reaction vessel. The solution is then refluxed to circulate water vapor over the molecular sieves. After the solution of 6-HQ phenolate has been dehydrated, the tetrazole is added to the solution to react with the 6-HQ phenolate to produce cilostazol.

In the process of Nishi et al., it was necessary to separate unreacted starting materials and the organic base by column chromatography. It is desirable in a large scale process to avoid chromatography and concomitant production of spent solid phase. We have further discovered that cilostazol prepared according to the teachings of the present invention or by other methods can be selectively crystallized from certain solvents in high purity without the need for "clean up" chromatography to remove, for example, unreacted starting materials. Suitable recrystallization solvents are 1-butanol, acetone, toluene, methyl ethyl ketone, dichloromethane, ethyl acetate, methyl t-butyl ether, dimethyl acetamide-water mixtures, THF, methanol, isopropanol, benzyl alcohol, 2-pyrrolidone, acetonitrile, Cellosolve, monoglyme, isobutyl acetate, sec-butanol, tert-butanol, DMF, chloroform, diethyl ether and mixtures thereof.

The purity of the cilostazol may be detected by any means known in the art, including, for example, high performance liquid chromatography (HPLC), such as reversed-phase HPLC (RP-HPLC) using gradient elution. As is known in the art, gradient elution involves steady changes in the mobile phase composition during the chromatographic run. For determining the purity of cilostazol crystalized according to the present invention, a RP-8 column should be used. The eluent components of the mobile phase are water and acetonitrile and the mobile phase is preferably controlled by a gradient program starting with an initial element of 100% water until a 1:1 ratio of the two components is obtained. The chromatographic system is equipped with an ultraviolet detector set at 254 nanometers. This RP-HPLC method allows the detection of cilostazol-related impurities until a level of at least 0.02% relative to the sample concentration.

In a further aspect of the present invention, when a pharmaceutical composition comprising cilostazol prepared according to the present invention is formulated for oral administration, the compound is preferably processed to have a reduced small particle size. Methods of obtaining reduced particle size of a compound are well known in the art and include, for example, processes such as fine-milling and micronization. Accordingly, in one embodiment of the present invention, the cilostazol prepared according to the present invention is fine-milled under suitable conditions of mill rotation rate and feed rate to where 90% of the particles have a diameter of about 60 microns. In another embodiment, the cilostazol is micronized by being passed through an air jet mill at a suitable feed air pressure, grinding air pressure, feed rate, and rotation rate to where 90% of the particles have a diameter equal to or less than about 15 microns. The cilostazol may then be formulated into a pharmaceutical composition or dosage form further comprising one or more pharmaceutically acceptable excipients. Such compositions and dosage forms include, for example, compacted tablets, powder suspensions, capsules, and the like.

The invention will now be further illustrated with the following examples, which offer highly specific procedures that may be followed in practicing the invention but which should not be construed as limiting the invention in any way.

EXAMPLES

Example 1

Preparation of Cilostazol Using A Phase Transfer Catalyst

A 1 L reactor was charged with 6-HQ (16.5 g, 0.1011 moles), and NaOH (1 eq.) in water (90 ml). To this solution was add toluene (15 ml) and CHCBT (22.22 g, 0.0915 moles), $Na_2SO_4$ (17 g) and catalyst (1.9 g) (aliquat 336). The mixture was heated to reflux for 8 h. After this period of time, the mixture was cooled to room temperature, the solid was filtered and washed with water and methanol to afford the crude product (29 g, yield 88%; purity by reversed-phase HPLC using gradient elution ~99%).

Example 2

Preparation of Cilostazol with Addition of CHCBT in One Portion

6-HQ (10 g, 0.0613 moles), KOH (4.05 g, 0.0722 moles), $K_2CO_3$ (1.5 g, 0.011 mole), CHCBT (18 g, 0.0742 moles) and n-BuOH (130 ml) were heated at reflux for ~5 hours. After cooling of the reaction mixture to room temperature the solid was filtered, washed with n-BuOH and water. The crude product (19.7 g, 85% yield, 98.7% pure) was recrystallized from n-BuOH (10 vol.) to give cilostazol crystals (yield 94%, 99.6% pure).

Example 3

Preparation of Cilostazol by Addition of the Base in Portions

6-HQ (10 g, 0.0613 moles), KOH (1.01 g, 0.018 mole), $K_2CO_3$ (1.5 g, 0.011 mole), CHCBT (13.4 g, 0.0552 moles) and 130 ml n-BuOH were heated at reflux for 1 hour. After 1 hour, a second 1.1 g portion of KOH was added and the reflux was continued. The procedure was repeated with two additional 1.1 g portions of KOH. After the addition of the whole KOH the reaction was continued for an additional hour. The reaction mixture was cooled to room temperature, the solid was filtered and washed with n-BuOH and dried to afford the product (15.6 g, 56% yield, 98.3% pure).

Example 4

Preparation of Cilostazol Using Molecular Sieves as Dehydrating Agent

A three neck flask equipped with condenser and a soxlet extraction funnel containing molecular sieves 3 Å (28 g) was charged with 6-HQ (10 g, 0.0613 moles), KOH (4.05 g, 0.0722 moles) and $K_2CO_3$ (1.5 g, 0.011 moles) and 130 ml n-BuOH. The mixture was heated to reflux and the reflux was maintained passing the solvent over the molecular sieves. After 30 minutes, CHCBT (18 g, 0.0742 moles, 1.2 equivalents) was added and the reflux was continued for about 5 h. Then, the reaction mixture was cooled and the product was filtered and washed with n-BuOH. The yield after drying was 14.4 g (62%, 98.3% pure).

Example 5

Preparation of Cilostazol Using an Excess of 6-HQ

6-HQ (10 g, 0.0613 moles), KOH (4.05 g, 0.0722 moles), $K_2CO_3$ (1.5 g, 0.011 mole), CHCBT (13.4 g, 0.0552 moles) and 130 ml n-BuOH were heated at reflux for 5 hours. After cooling of the reaction mixture to room temperature the solid was filtered and washed with n-BuOH and water; the material was dried to give the product cilostazol (15.93 g, 76.2% yield, 98.5% pure).

Example 6

Crystallization of Cilostazol from Recrystallization Solvents

Table 1 provides conditions for selectively crystallizing cilostazol from mixtures containing minor amounts of 6-HQ and CHCBT and obtaining substantially pure cilostazol.

TABLE 1

| Example | Solvent | Volume* | Recommended Procedure | Purity |
|---|---|---|---|---|
| 6 | n-BuOH | 10 | | 97.2 |
| 7 | n-BuOH | 20 | | 98.1 |
| 8 | Acetone | 20 | Slurry. Reflux. Cool to r.t. | 98.65 |

TABLE 1-continued

| Example | Solvent | Volume* | Recommended Procedure | Purity |
|---|---|---|---|---|
| 9 | Toluene | 20 | Dissolve at reflux. Cool to r.t. | 98.60 |
| 10 | Methyl ethyl ketone | 11 | Dissolve at reflux. Cool to r.t. | 99.33 |
| 11 | $CH_2Cl_2$ | 4 | Dissolve at reflux. Cool to r.t. | 98.82 |
| 12 | Ethyl acetate | 10 | Slurry at reflux 1 h. Cool to r.t. | 97.50 |
| 13 | MTBE | 10 | Slurry at reflux 1 h. Cool to r.t. | 94.06 |
| 14 | 2:1 DMA-H2O | 10 | Dissolve in DMA at ~70–80° C.. Add water. Cool to r.t. Precipitate at 65° C. | |
| 15 | THF | 13 | Dissolve at reflux. Cool to r.t. | |
| 16 | Methanol | 3 | Dissolve at reflux. Cool to r.t. Precipitate at 55° C. | 99.16 |
| 17 | Acetone | 2.5 | Slurry at reflux for 1 h. Cool to r.t. | 99.12 |
| 18 | Ethanol | 12.5 | Dissolve at reflux. Cool to r.t. | 98.90 |
| 19 | Isopropanol | 19 | Dissolve at reflux. Cool to r.t. | 98.75 |
| 20 | Acetone | 33 | Dissolve at reflux. Cool to 40° C. | 98.90 |
| 21 | Benzyl alcohol | 2 | Dissolve at 55° C.. Cool to r.t. | 98.85 |
| 22 | 2-Pyrrolidone | 3.5 | Dissolve at 65° C.. Cool to r.t. | |
| 23 | Acetonitrile | 6.5 | Dissolve at reflux. Cool to 30° C. | 98.70 |
| 24 | 2-BuOH | 5 | Dissolve at ~90° C.. Cool to r.t. | 94.80 |
| 25 | Cellosolve | 3 | Dissolve at ~100° C.. Cool to r.t. | 98.80 |
| 26 | Monoglyme | 13 | Dissolve at reflux. Cool to r.t. | 97.06 |
| 27 | iso-butyl-acetate | 23 | Dissolve at reflux (115° C.). Cool to r.t. | 97.50 |
| 28 | n-BuOH | 20 | Dissolve at reflux. Treat with decolorizing agents, (SX1 activated carbon and tonsil silicate). Cool to r.t. | 99.14 |
| 29 | MeOH | 10 | Dissolve at reflux. Cool to r.t. | 99.92 |
| 30 | MeOH | 10 | Dissolve at reflux. Cool to r.t. | 99.93 |
| 31 | MeOH | 10 | Dissolve at reflux. Cool to r.t. | 99.95 |

*Relative to the volume of cilostazol

Example 32

Reduction of Particle Size and Particle Size Distribution of Cilostazol

Cilostazol obtained from Examples 1–6, is fine-milled by being passed through a pin mill at a mill rotation rate of 10500 rpm and a feed rate of 15 kg/hr to where 90% of the cilostazol particles have a diameter of about 60 microns.

Example 33

Cilostazol is micronized by being passed through an air jet mill at a feed rate of 20 kg/hr, a feed air pressure of 7 bars, a grinding air pressure of 4 bars to where 90% of the cilostazol particles have a diameter of less than about 15 microns. The rotation rate of the jet mill is 300 mm.

It should be understood that some modification, alteration and substitution is anticipated and expected from those skilled in the art without departing from the teachings of the invention. Accordingly, it is appropriate that the following claims be construed broadly and in a manner consistent with the scope and spirit of the invention.

We claim:

1. A process for preparing cilostazol comprising:
   a) combining 6-hydroxy-3,4-dihydroquinolinone and at least one alkali metal carbonate;
   b) removing water using molecular sieves;
   c) adding 1-cyclohexyl-5-(4-halobutyl)-tetrazole; and
   d) recovering cilostazol.

2. The process according to claim 1, wherein the alkali metal carbonate is sodium carbonate or potassium carbonate.

3. The process according to claim 1, wherein the alkali metal carbonate is potassium carbonate.

4. The process according to claim 1, wherein the molecular sieves have a size of three or four angstroms.

5. The process according to claim 1, wherein the molecular sieves have a size of three angstroms.

6. The process according to claim 1, further comprising a solvent selected from the group consisting of 1-butanol, isopropanol, 2-butanol, and amyl alcohol.

7. The process according to claim 6, wherein removing water is performed by placing the molecular sieves in a soxlet extraction funnel or a reservoir of a dropping funnel and heating to reflux to allow water vapor to circulate through the sieves.

8. The process according to claim 1, wherein the 1-cyclohexyl-5-(4-halobutyl)-tetrazole is present in about 0.9 to about 0.99 equivalents with respect to 6-hydroxy-3,4-dihydroquinolinone.

* * * * *